United States Patent [19]

Wirtz et al.

[11] Patent Number: 5,292,931
[45] Date of Patent: Mar. 8, 1994

[54] CARRIER CATALYST, PROCESS FOR ITS PREPARATION, AND ITS USE FOR THE PREPARATION OF VINYL ACETATE

[75] Inventors: Peter Wirtz, Königstein; Karl-Fred Wörner, Eschborn; Friedrich Wunder, Hattersheim am Main; Klaus Eichler, Eschborn; Günter Roscher, Kelkheim, all of Fed. Rep. of Germany; Ioan Nicolau, Corpus Christi, Tex.

[73] Assignee: Hoechst Aktiengesellschaft, Frankfurt am Main, Fed. Rep. of Germany

[21] Appl. No.: 44,212

[22] Filed: Apr. 7, 1993

Related U.S. Application Data

[62] Division of Ser. No. 900,839, Jun. 18, 1992, Pat. No. 5,250,487.

[30] Foreign Application Priority Data

Jun. 21, 1991 [DE] Fed. Rep. of Germany ....... 4120492

[51] Int. Cl.⁵ .............................. C07C 67/05
[52] U.S. Cl. ................................... 560/245
[58] Field of Search .......................... 560/245

[56] References Cited

U.S. PATENT DOCUMENTS

| 3,775,342 | 11/1973 | Kronig et al. |
| 3,939,199 | 2/1976 | Fernholz et al. |
| 4,048,096 | 9/1977 | Bissot |
| 4,668,819 | 5/1987 | Fernholz et al. |
| 4,902,823 | 2/1990 | Wunder et al. |

FOREIGN PATENT DOCUMENTS

| 2018991 | 12/1990 | Canada |
| 2031429 | 6/1991 | Canada |
| 0431478 | 6/1991 | European Pat. Off. |
| 0464633 | 1/1992 | European Pat. Off. |
| 3919524 | 12/1990 | Fed. Rep. of Germany |
| 1117595 | 6/1968 | United Kingdom |

*Primary Examiner*—Michael L. Shippen

[57] ABSTRACT

The invention relates to a process for the preparation of a catalyst which contains palladium and/or compounds thereof and alkali metal compounds, and additionally cadmium compounds and/or gold and/or compounds thereof, on support particles which have been pressed from $SiO_2$ or an $iO_2$-$Al_2O_3$ mixture with the aid of a binder which comprises a) washing the roasted support particles with an acid which does not react with $SiO_2$ or $SiO_2$-$Al_2O_3$ mixtures, until no further cations of the binder employed during pressing of the support particles are released from the support particles;
b) then impregnating the support particles with palladium, and gold or cadmium;
c) then bringing the impregnated support particles into contact with a solution of a base at least until the thickness of the nobel metal shell generated in this way on the support particles no longer changes substantially; and
d) then impregnating the support particles with an alkali metal compound.

A shell-like distribution of the palladium and if appropriate of the gold in the support particles is generated in this manner.

Furthermore, the invention relates to a catalyst prepared in this way and to its use for the preparation of vinyl acetate.

5 Claims, No Drawings

CARRIER CATALYST, PROCESS FOR ITS PREPARATION, AND ITS USE FOR THE PREPARATION OF VINYL ACETATE

This application is a division of our copending application Ser. No. 07/900,839, filed Jun. 18, 1992, now U.S. Pat. No. 5,250,487.

It is known that ethylene can be reacted in the gas phase with acetic acid and oxygen or oxygen-containing gases over catalysts to give vinyl acetate. Suitable catalysts contain palladium and/or compounds thereof and alkali metal compounds, and additionally cadmium compounds and/or gold and/or compounds thereof. The preferred alkali metal compounds are potassium compounds (U.S. Pat. Nos. 3,939,199 and 4,668,819). These active components are applied to supports, silicic acid or aluminum oxide in general being used as the support material.

U.S. Pat. Nos. 4,048,096 and 3,775,342 describe a special form of distribution of the noble metals, in which the noble metals are present in a shell on the support particles, while the core of the particles is largely free from noble metals. An increased specific yield (g of vinyl acetate/g of noble metal) is obtained by this measure. The distribution of the noble metals in the form of a shell is achieved by impregnation and subsequent precipitation of the noble metals with alkaline compounds.

According to U.S. Pat. No. 3,939,199, the total pore volume of a highly efficient support should be 0.4–1.2 ml/g, and less than 10% of this volume should be formed by "micropores" having a pore diameter of less than 30 Å (Angström). Such supports can be prepared from aerogenic $SiO_2$ or an aerogenic $SiO_2$-$Al_2O_3$ mixture which is present in the form of vitreous microbeads, which can be prepared, for example, by flame hydrolysis of silicon tetrachloride or a silicon tetrachloride-aluminum trichloride mixture in an oxyhydrogen gas flame. These microbeads are commercially available under the name ®Aerosil or ®Cabosil.

DE-OS 39 19 524 describes a support of the type just mentioned, which comprises of $SiO_2$ or an $SiO_2$-$Al_2O_3$ mixture having a surface area of 50-250 $m^2$/g and a pore volume of 0.4-1.2 ml/g, the particles of which have a particle size of 4 to 9 mm, 5 to 20% of the pore volume of the support being formed by pores having radii of 200 to 3000 Å and 50 to 90% of the pore volume being formed by pores having radii of 70 to 100 Å.

According to EP-A-0 431 478, shaped articles, i.e. shaped support particles, are then advantageously prepared from the microbeads, for example by tablet-making or extrusion, with the addition of one or more carboxylates of Li, Mg, Al, Zn, Fe or Mn as binders and with the addition of organic fillers (such as sugars, urea, higher fatty acids, longer-chain paraffins or microcrystalline cellulose) and lubricants (such as kaolin, graphite or metal soaps). The shaped articles are then roasted in $O_2$-containing gases.

Attempts to generate a noble metal shell on these shaped articles, which have been pressed with a binder, by impregnating with noble metals and then treating them with an alkaline compound fail. Instead, a homogeneous noble metal distribution in the entire shaped article is obtained.

It has now been found, surprisingly, that a shell-like noble metal distribution is obtained if, before the impregnation with noble metal, the shaped articles are washed with an acid until no further cations of the binder (Li, Mg, Al, Zn, Fe or Mn) are washed out.

The invention relates to a process for the preparation of a catalyst which contains palladium and/or compounds thereof and alkali metal compounds, and additionally cadmium compounds and/or gold and/or compounds thereof, on support particles which have been pressed from $SiO_2$ or an $SiO_2$-$Al_2O_3$ mixture with the aid of a binder consisting of one or more Li, Mg, Al, Zn, Fe or Mn salts of a $C_2$-$C_{26}$-carboxylic acid and have subsequently been roasted in oxygen-containing gases at 500°–900° C. for a period of 0.25–5 hours, and thereafter have a surface area of 50-250 $m^2$/g and a pore volume of 0.4–1.2 ml/g at a particle size of 1-15 mm, 5-20% of the pore volume being formed by pores having a radius of 200-3000 Å and 50-90% of the pore volume being formed by pores having a radius of 70-100 Å, which comprises a) washing the roasted support particles with an acid which does not react with $SiO_2$ or $SiO_2$-$Al_2O_3$ mixtures, until no further cations of the binder employed during pressing of the support particles are released from the support particles;
b) then impregnating the support particles with palladium, and gold or cadmium;
c) then bringing the impregnated support particles into contact with a solution of a base at least until the thickness of the noble metal shell generated in this way on the support particles no longer changes substantially; and
d) then impregnating the support particles with an alkali metal compound.

Furthermore, the invention relates to a catalyst prepared in this way, and to the use of said catalyst for the preparation of vinyl acetate from ethylene, acetic acid and oxygen in the gas phase.

Because of the distribution of the noble metals in the form of a shell which is achieved in this manner, these are more readily accessible for the reaction, which means that better specific yields are achieved than in the case of a homogeneous distribution. Either more vinyl acetate can therefore be produced for the same amount of noble metal in the catalyst than in the case of homogeneous distribution, or the noble metal content of the catalyst can be decreased for the same amount produced, and hence costs can be saved. It is particularly surprising here that in spite of the acid washing, in which the binder is removed almost completely, the mechanical ability of the support does not suffer.

The content of palladium on the shell type catalyst is in general 0.5–2.5% by weight, preferably 0.7–1.8% by weight, in particular 1.0–1.6% by weight, based on the total weight of the supported catalyst. If gold is additionally applied, its content is 0.2–0.7% by weight, based on the total weight of the supported catalyst.

The alkali metal compounds employed as activators are in general applied in an amount of 0.5–5% by weight, based on the total weight of the catalyst.

If cadmium is used as an additional activator, its content is 0.5–5% by weight, based on the total weight of the catalyst.

The percentage figures stated always relate to the amounts of the elements palladium, gold, alkali metal and cadmium present on the catalyst; any anions are not included in the calculation.

The following catalysts are preferred:

Palladium/cadmium/potassium and palladium/gold/potassium, it being possible for the palladium and gold to be present on the finished catalyst in the form of metals or compounds.

The preparation of the shell-type catalysts is divided into the following steps:

Vitreous microbeads are first produced, for example by flame hydrolysis of silicon tetrachloride or a silicon tetrachloride-aluminum trichloride mixture in an oxyhydrogen gas flame (U.S. Pat. No. 3 939 199). Microbeads which have a surface area of 150–250 m$^2$/g and consist of at least 95% by weight of SiO$_2$ and not more than 5% by weight of Al$_2$O$_3$ are particularly suitable.

Shaped articles are then produced from the microbeads with the addition of one or more C$_2$–C$_{26}$-carboxylates of Li, Mg, Zn, Al, Fe or Mn as binders and with the addition of organic fillers (such as sugars, urea, higher fatty acids, longer-chain paraffins or microcrystalline cellulose) and lubricants (such as kaolin, graphite and metal soaps). Preferred binders are salts of Mg, Al, Li or Fe, in particular salts of Mg or Al, with C$_5$–C$_{22}$-carboxylic acids, but above all C$_{10}$–C$_{20}$-carboxylic acids. The carboxylate or carboxylates are in general employed in amounts such that the sum of the amounts of Li, Mg, Zn, Al, Fe and Mn (calculated as elements) is 0.1 to 5% by weight, based on the support material, preferably 0.3 to 1.5% by weight. The shaped articles are then roasted in O$_2$-containing gases at about 500°–900° C. for about 0.25–5 hours to remove the carbon introduced with these additives. The surface area of the support, its pore volume and the proportion of the pore volume formed by pores of a certain radius (pore radius distribution) is determined by the nature of the shaping, the temperature and duration of the roasting, the relative amounts of binders, fillers, lubricants and microbeads and by the surface area of these microbeads. These parameters are to be chosen such that, after roasting, the shaped articles have a surface area of 50–250 m$^2$/g and a pore volume of 0.4–1.2 ml/g at a particle size of 1–15 mm, 5–20% of the pore volume being formed by pores having a radius of 200–3000 Å and 50–90% of the pore volume being formed by pores having a radius of 70–100 Å.

The particle size is preferably 4–9 mm, particularly preferably 5–7 mm, it being possible for beads, tablets or particles with other shapes to be used as the shaped articles.

All the acids which do not react with SiO$_2$ or SiO$_2$-Al$_2$O$_3$ mixtures and have cations—if these have a deactivating action (such as sulfate or chloride)—which can be removed from the support by washing out can be used for acid washing of the roasted shaped articles (i.e. the roasted and pressed support particles).

Preferred acids are mineral acids, such as hydrochloric acid, sulfuric acid, phosphoric acid or nitric acid, and hydrochloric acid is particularly preferred. The acids can be employed in either concentrated or dilute form. It is also possible to use mixtures of different acids. The acid wash is carried out until no further cations are released from the binder. This can be determined by removing the support from the acid after a certain period of time and then washing it in fresh acid; if cations from the binder are no longer detectable in this acid, the treatment time was sufficient. The duration of the acid treatment depends inter alia on the nature of the acid and on the degree of dilution; dilute acids generally require a longer treatment time. The acids are preferably 5–50% strength acids, particulary preferably 10–20% strength acids. The nature and amount of the binder and the temperature during the acid wash furthermore also play a role. A treatment time of 10–14 hours is in general sufficient for the particularly preferred embodiment of the acid wash using 10–20% strength hydrochloric acid. The amount of acid employed is preferably chosen so that the catalyst is completely covered with liquid.

After the acid wash, the anions of the acid are washed out if they would be harmful to the catalyst (such as chloride ions or sulfate ions); this is most easily effected by washing the support with running distilled water until anions are no longer detected by customary analytical methods (for example precipitation with silver nitrate for chloride or precipitation with barium chloride for sulfate). Preferably, however, washing with water is also carried out in the case of acids having anions which are harmless to the catalysis.

Before the impregnation of the support with palladium and gold or cadmium which now follows, the support is preferably dried. The impregnation is preferably carried out by adding to the support material salts of the metals mentioned dissolved in a solvent. Water or alcohols, such as methanol or ethanol, are particularly suitable solvents. The amount of solvent advantageously corresponds to the integral pore volume of the support.

Possible compounds of palladium are all the salts and complexes which are soluble and leave behind no deactivating substances in the finished catalyst (washed, if necessary, as described above). Chloride or other soluble salts which are accessible to a precipitation as (hydrated) oxide, such as nitrate, oxalate and sulfate, are particularly suitable.

Gold chloride or the soluble salts of tetrachloroauric acid are particularly suitable gold compounds.

Possible cadmium compounds are the compounds which are soluble, for example carboxylate, oxide, hydroxide, carbonate, chloride, citrate, tartrate, nitrate, acetylacetonate and acetoacetate.

The base treatment of the impregnated support, which is preferably dried again first, is now carried out. Possible bases are, in particular, alkali metal hydroxides, alkali metal silicates and alkali metal carbonates, alkali metal hydroxides are preferred and potassium hydroxide and sodium hydroxide are particularly preferred. Mixtures of different bases can also be employed. The base should be dissolved in a solvent in which the compounds of Pd and Au or Cd employed in the impregnation are also soluble; possible solvents are, for example, water and alcohols. To avoid losses of noble metal during the base treatment, the volume of the solvent should preferably correspond to the integral pore volume of the support; however, it is also possible to employ larger amounts of solvent. The amount of base needed is obtained from the stoichiometrically calculated amounts of hydroxide ions which are needed to convert the palladium and the gold or cadmium into the hydroxides; it proves advantageous to use an excess of base, for example 100–200% of the stoichiometrically required amount, preferably 105–150% of the stoichiometrically required amounts and particularly preferably 110–140% of the stoichiometrically required amount. The support must remain in contact with the base at least until the thickness of the noble metal shell generated no longer changes substantially. This can easily be ascertained by removing catalyst particles after certain intervals of time and cutting them open. The duration of the treatment with the base depends on the concentration thereof and the ambient temperature, the treatment preferably being carried out at room temperature. In the preferred case of the use of potassium hydroxide or sodium hydroxide in water, a treatment time of about 6 hours is in general sufficient; however, longer treatment is in general harmless. If the salts employed during the impregnation with palladium and gold or cadmium contained constituents harmful to the catalyst (for example chloride or sulfate), the catalyst is now washed with running distilled water until these deactivating substances are no longer detectable.

The catalyst can now be reduced, for example with a solution of hydrazine hydrate or by passing over reducing gases, such as ethylene or methanol, at room temperature or elevated temperature, the reducing gas advantageously being diluted with an inert gas, such as nitrogen. The amount of reducing agent depends on the amount of palladium and if appropriate of gold employed; the reduction equivalent should be at least 1–1.5 times the oxidation equivalent, but larger amounts do no harm.

After the base treatment, or if appropriate after the reduction, the alkali metal compound is applied to the catalyst; the catalyst is preferably dried beforehand. The alkali metal compound is dissolved in a suitable solvent, for example water or alcohol, the amount of solvent preferably corresponding to the integral pore volume of the support material to be impregnated. The alkali metal compounds employed can be carboxylates, for example potassium acetate, sodium acetate or sodium propionate. Other alkali metal salts, such as hydroxides, oxides or carbonates, are also suitable if they are converted into the acetates under the reaction conditions. Potassium compounds, in particular, potassium acetate, are preferably employed.

The catalyst should preferably be dried before being introduced into the reactor.

The vinyl acetate is in general prepared by passing acetic acid, ethylene and oxygen or oxygen-containing gases over the finished catalyst at temperatures of 100°–220° C., preferably 120°–200° C., under pressures of 1–25 bar, preferably 1–20 bar, it being possible for unreacted components to be passed in circulation. Because of the known flammability limits, the oxygen concentration should not exceed 10% by volume, based on the acetic acid-free mixture. Under certain circumstances, dilution with inert gases is advantageous, nitrogen or carbon dioxide, for example, being suitable.

The following examples are intended to illustrate the invention.

COMPARISON EXAMPLE 1

A support was first prepared from $SiO_2$ microbeads having a surface area of 200 m²/g with 10% by weight of magnesium stearate as the binder. The finished support contained 0.4% by weight of Mg. The surface area was 186 m²/g and the pore volume was 0.8 ml/g, 78% of the pore volume being formed by pores having a radius of 70–100 Å and 16% of the pore volume being formed by pores having a radius of 200–3000 Å. The support particles had the shape of cylinders with domed front faces (6 mm diameter and 6 mm height).

100 g of the support were impregnated with a solution (corresponding to the pore volume of the support) of 11.5 g of Pd acetate, 10.0 g of Cd acetate and 10.8 g of K acetate in 66 ml of glacial acetic acid and dried to a residual solvent content of 2% by weight at 60° C. under nitrogen and under a pressure of 200 mbar. This resulted in a doping of 2.3% by weight of Pd, 1.8% by weight of Cd and 2.0% by weight of K.

50 ml of the finished, homogeneously impregnated catalyst were introduced into a reaction tube having an internal diameter of 8 mm and a length of 1.5 m. The reaction gas consisting of 27% by volume of ethylene, 55% by volume of nitrogen, 12% by volume of acetic acid and 6% by volume of oxygen was passed over the catalyst under a pressure of 8 bar at the reactor intake and at a catalyst temperature of 150° C. The results can be seen from the table.

COMPARISON EXAMPLE 2

The same support as in Comparison Example 1 was impregnated with a solution of 2.6 g of Pd chloride and 3.3 g of Cd chloride in 83 ml of water. After drying, 1.5 g of NaOH in 83 ml of water were added and the mixture was stirred for 6 hours. After the catalyst had been left to stand at room temperature for 16 hours, it was washed with a large quantity of water and then dried. Thereafter, it was impregnated with a solution of 12.5 g of K acetate in 83 ml of water and dried again. A homogeneously impregnated catalyst with a doping of 1.5% by weight of Pd, 2.0% by weight of Cd and 5.0% by weight of K was obtained. Testing was carried out as in Comparison Example 1.

COMPARISON EXAMPLE 3

The same support as in Comparison Example 1 was impregnated with a solution of 2.8 g of $Na_2PdCl_4$ and 0.7 g of $HAuCl_4$ and dried. After precipitation with 1.1 g of aqueous NaOH, the catalyst was washed with a large quantity of water and dried. After impregnation with an aqueous solution of 7.0 g of K acetate, the catalyst was dried again. The catalyst contained 1.0% by weight of Pd, 0.4% by weight of Au and 2.8% by weight of K. No shell was present, i.e. the catalyst was impregnated homogeneously again. Testing was carried out in a Berty reactor at 154° C. using a gas mixture of 8% of $O_2$, 37.5% of $C_2H_4$, 15.7% of HOAc and 38.8% of $N_2$.

EXAMPLE 1

The catalyst was prepared as in Comparison Example 2, with the exception that, before the impregnation with palladium chloride and cadmium chloride, the support was brought into contact with 10% strength hydrochloric acid at room temperature for 14 hours and was subsequently washed free from chloride under running water and then dried. A shell-type catalyst was obtained. The residual content of binder cations (Mg) was 0.01%. Testing was carried out as in Comparison Example 1.

EXAMPLE 2

The catalyst was prepared as in Comparison Example 3, with the exception that, before the impregnation with palladium salts and gold salts, the support was washed with hydrochloric acid as in Example 1 and then washed free from chloride with water and dried. The resulting shell-type catalyst was tested as in Comparison Example 3.

TABLE

| | Comparison Example | | | Example | |
|---|---|---|---|---|---|
| | 1 | 2 | 3 | 1 | 2 |
| STY (g of vinyl | 773 | 440 | 657 | 752 | 698 |

TABLE-continued

|  | Comparison Example | | | Example | |
| --- | --- | --- | --- | --- | --- |
|  | 1 | 2 | 3 | 1 | 2 |
| acetate per liter of catalyst and per hour | | | | | |
| Specific yield (g of vinyl acetate per g of noble metal and per hour) | 67.2 | 58.7 | 93.9 | 100.3 | 99.7 |
| Combustion (%) | 14 | 16 | 12.5 | 7.8 | 11.2 |
| Ethyl acetate content (ppm) | 260 | 260 | 314 | 120 | 222 |

"STY" denotes the space-time yield
"Combustion" denotes the percentage of ethylene reacted which is converted into $CO_2$;
"Ethyl acetate content" relates to the content of ethyl acetate in the condensed reaction products.

We claim:
1. A process for the preparation of vinylacetate, comprising:
   bringing a gas phase comprising ethylene, acetic acid, and oxygen or an oxygen containing gas into contact with a catalyst which contains:
   palladium and/or compounds thereof and alkali metal compounds, and additionally cadmium compounds and/or gold and/or compounds thereof, on support particles which have been pressed from $SiO_2$ or an $SiO_2$-$Al_2O_3$ mixture with the aid of a binder comprising one or more Li, Mg, Al, Zn, Fe or Mn salts of a $C_2$-$C_{26}$-carboxylic acid and have subsequently been roasted in oxygen-containing gases at 500°-900° C. for a period of 0.25-5 hours, and thereafter have a surface area of 50-250 $m^2/g$ and a pore volume of 0.4-1.2 ml/g at a particle size of 1-15 mm, 5-20% of the pore volume being formed by pores having a radius of 200-3000 Å, and 50-90% of the pore volume being formed by pores having a radius of 70-100 Å, said catalyst having been prepared by the steps comprising:
   a) washing the roasted support particles with an acid which does not react with $SiO_2$ or $SiO$-$Al_2O_3$ mixtures, until no further cations of the binder employed during pressing of the support particles are released from the support particles;
   b) then impregnating the support particles with palladium, and gold or cadmium;
   c) then bringing the impregnated support particles into contact with a solution of a base at least until the thickness of the noble metal shell generated in this way on the support particles no longer changes substantially; and
   d) then impregnating the support particles with an alkali metal compound.
2. The process as claimed in claim 1, wherein hydrochloric acid, sulfuric acid, phosphoric acid or nitric acid is used as the acid in step a).
3. The process as claimed in claim 1, wherein hydrochloric acid is used as the acid in step a).
4. The process as claimed in claim 1, wherein an alkali metal hydroxide is used as the base in step c).
5. The process as claimed in claim 1, wherein a potassium compound is employed in step d).

* * * * *